United States Patent
Kim et al.

Patent Number: 5,641,388
Date of Patent: Jun. 24, 1997

[54] METHOD AND APPARATUS FOR ELECTROLYZING BY USING VERTICAL CIRCULATING CAPILLARY TUBE TYPE MERCURY BUNDLED ELECTRODE

[75] Inventors: Kwang-Wook Kim; Eil-Hee Lee; Young-Joon Shin; Jae-Hyun Yoo, all of Daejeon-Si, Rep. of Korea

[73] Assignee: Korea Atomic Energy Research Institute, Daejeon-Si, Rep. of Korea

[21] Appl. No.: 572,709

[22] Filed: Dec. 14, 1995

[30] Foreign Application Priority Data

Jun. 5, 1995 [KR] Rep. of Korea ............... 95-14823

[51] Int. Cl.$^6$ ............... C25B 15/00; C25B 9/00; C25B 11/00
[52] U.S. Cl. ............... 204/250; 204/229; 204/251; 204/280
[58] Field of Search ............... 204/229, 250, 204/280, 292, 413, 251, 219, 220; 205/560, 587

[56] References Cited

U.S. PATENT DOCUMENTS

| | | | |
|---|---|---|---|
| 3,065,163 | 11/1962 | Honsberg | 204/220 |
| 3,449,234 | 6/1969 | Csizi | 204/220 |
| 3,481,856 | 12/1969 | Csizi | 204/250 |
| 4,046,663 | 9/1977 | Fleet et al. | 204/280 |
| 4,091,829 | 5/1978 | Cotton | 204/220 |
| 4,440,614 | 4/1984 | Reynolds et al. | 204/219 |
| 4,661,210 | 4/1987 | Tenygl | 205/789.5 |
| 5,126,023 | 6/1992 | Huang et al. | 204/180.1 |

OTHER PUBLICATIONS

Electrochemical Cells, *Experimental Electrochemistry For Chemists*, John Wiley & Sons, 1974, pp. 150–151. (no month).

*Primary Examiner*—Kathryn L. Gorgos
*Assistant Examiner*—Edna Wong
*Attorney, Agent, or Firm*—Armstrong, Westerman, Hattori, McLeland & Naughton

[57] ABSTRACT

An electrolyzing apparatus using a circulating capillary tube type mercury bundled electrode is disclosed, in which the advantage of mercury that it has a high overpotential for hydrogen evolution reaction compared with the general solid metals is preserved, and the disadvantage of mercury that it cannot be so shaped as to have a large contact area is overcome. That is, the mercury contact area is maximized. The oxidation and reduction reactions which occur in the vertically circulating capillary tube type mercury bundle electrode electrolyzing apparatus can be defined by a simple formula so as to quantize their analysis. Based on this formula, the stability checking, and the adjustment of the oxidation state of metal ions in the solution can be carried out in a rapid and continuous manner. Further, the concentration of the metal ions and the oxidation state of the metal ions within the solution can be analyzed in the same manner.

4 Claims, 5 Drawing Sheets

5,641,388

METHOD AND APPARATUS FOR ELECTROLYZING BY USING VERTICAL CIRCULATING CAPILLARY TUBE TYPE MERCURY BUNDLED ELECTRODE

FIELD OF THE INVENTION

The present invention relates to an electrolyzing apparatus using a vertical circulating capillary tube type mercury bundled electrode. More specifically, the present invention relates to a method for manufacturing a capillary tube type mercury bundle electrode having a large surface area formed in a dense fiber bundle.

BACKGROUND OF THE INVENTION

If concentration and oxidation valence state of metal ions in an aqueous solution are to be analyzed, and if an electrolyzing reaction mechanism is to be studied, or if the metal ions are to be effectively separated and purified in a continuous process, then a rapid adjustment of the oxidation state of the metal ions in the solution is required. For these purposes, some electrolytic system with large electrode area in a simple structure, which can control the oxidation state of metal ions rapidly and continuously without adding chemicals into the system, is required.

In constituting a continuous electrolyzing apparatus, the most important factor is the selection of an electrode material which is stable in the working solution, superior in its repeatability, and affording a large contact electrode area within a small space. Another important factor is the simple manufacturing of the electrode with above described electrode material.

Generally, solid metals are widely used as the electrode of an electrolyzing apparatus, because the processing of them is easy in various shapes. However, most of them are easily oxidized in the air, and therefore, the reproduceability is lowered in repeated runs, as well as being lowered in the current density.

In order to prevent these phenomena, a precise surface polishing is performed or an electrochemical pre-treatment is carried out before using the solid metal electrode. Further, these solid metal electrodes are low in the overpotential against hydrogen evolution reaction, and therefore, hydrogen is generated near the reducing potential of the concerned elements, with the result that the interpretation of the electrolytic current is interfered. Further, in manufacturing an electrolyzing apparatus with a large contact electrode area of the solid metal, the structure becomes complicated, and the size of the apparatus is inevitably increased, with the result that the manufacturing cost is increased.

On the other hand, mercury, which is a liquid metal, has the highest overpotential for hydrogen evolution reaction among metal electrodes, and therefore, it is widely used in the research on a electroredox reaction mechanism. However, it has a drawback of difficult formation of a definite shape of large area due to its property of high surface tension. Therefore, the mercury electrode is usually used in shape of a droplet or a small pool for the electrochemical analysis, so that its surface can be used as an electrode area. The polarography using the mercury droplets as a working electrode is suitable for the electroredox study owing to the mercury droplet formed freshly and regularly through a capillary tube. However, due to its structure and to the restricted electrode area, it cannot be applied to a process in which a fast adjustment of oxidation state of metal ions is required. In order to raise the overpotential of the general solid metals against hydrogen evolution reaction, there are cases in which a thin film of mercury is coated on a metal body to use it as an electrode. However, due to the instability of the coated mercury, it is impossible to use the electrode for a long time.

SUMMARY OF THE INVENTION

The present invention is intended to overcome the above described disadvantages of the conventional techniques.

Therefore it is the object of the present invention to provide an electrolyzing apparatus using a circulating capillary tube type mercury bundled electrode, in which the advantage of mercury that it has a high overpotential for hydrogen evolution reaction compared with the general solid metals is preserved, and the disadvantage of mercury that it cannot be so shaped as to have a large contact area is overcome.

The basic conception of the present invention is as follows. That is, mercury tends to be broken into drops, because of its high surface tension. However, mercury is a liquid, and therefore, as shown in FIG. 1, if mercury is introduced into a fine fiber bundle packed densely within a fixed volume with pressure sufficient to overcome the surface tension of the mercury and drag force due to the mercury passing through the fiber bundle, then the capillary phenomenon occurs in mercury as in the case of the general fluid. Therefore, mercury maintains a continuity within the fiber bundle, and at the same time, it is widely spread.

Further, if an aqueous solution containing metal ions which requires to be reduced/oxidized at the mercury surface is fed into the capillary bundle at the same time, then the aqueous solution also is spread in the fiber bundle owing to the capillary phenomenon. And the solution is discharged from the fiber bundle together with the mercury, keeping well a large interfacial area between the mercury and the solution for the electroreaction.

FIG. 2 is a photograph of the spread mercury formed within the dense fiber bundle. In this photograph, fine mercury strips in a net form are seen through the well developed spaces between the thin fibers. Further, owing to the well developed countless mercury capillaries, the inner wall of the porous glass tube of the porous fiber bundle is shining.

The fibers which are used for manufacturing the capillary tube type mercury bundle has to be stable in an electrolytic solution. Further, it should be non-conductive, so that no electrolytic reaction would occur on the fiber surfaces. Further, the fibers should be sufficiently thin, so that the fibers can form extremely tiny capillary tubes within the porous glass tube. Further, more than a certain number of fibers has to be accommodated per unit cross sectional area, so that the capillary phenomena of mercury and solution would be well induced within the fixed space.

The glass tube serves as an outer shell for bundling the fibers. Further, it isolates the working solution from the counter solution, and serves as a membrane for maintaining an electrical neutrality during the electrolyzing reaction of the electrolyte.

FIG. 3 illustrates a process for carrying out an electrolysis using a vertical continuous capillary tube type mercury bundle electrode formed as described above.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above object and other advantages of the present invention will become more apparent by describing in detail the preferred embodiment of the present invention with reference to the attached drawings in which.

DESCRIPTION OF THE PREFERRED EMBODIMENT

Figure 1:
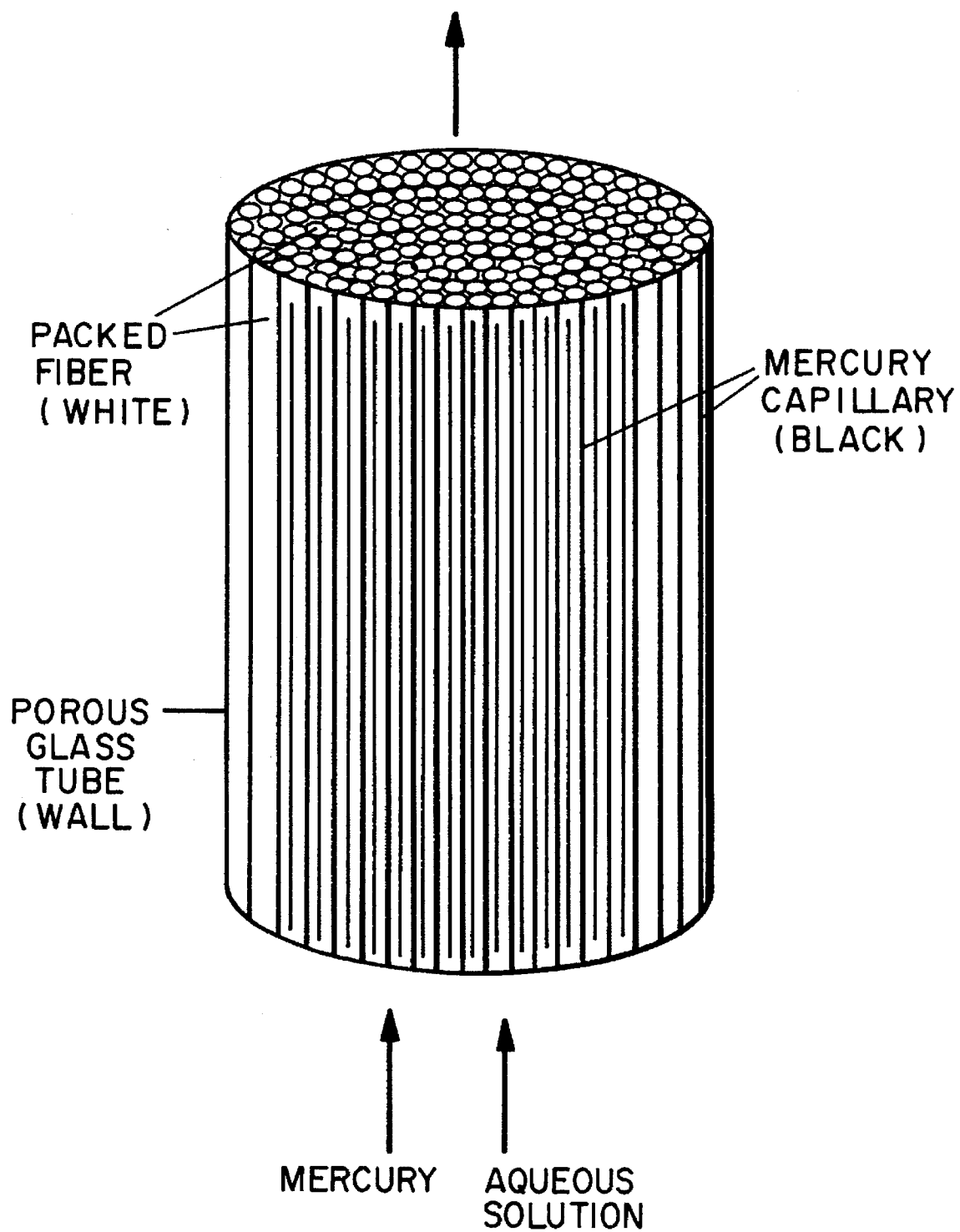
FIG. 1 is a conceptional view of the capillary tube type mercury bundle formed by a group of fibers packed densely into a porous glass tube so as to maximize the area of the mercury as a working electrode within an electrolyzing apparatus.
Figure 2:
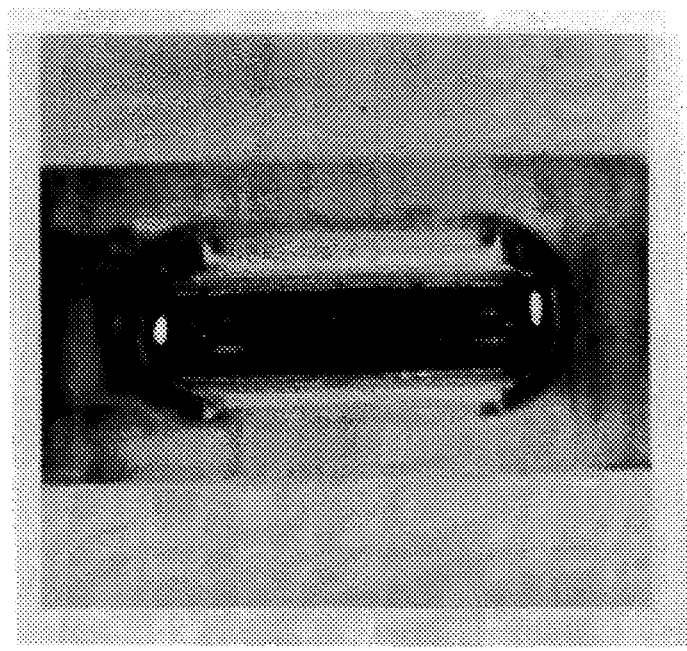
FIG. 2 is a photograph showing diffused mercury through the dense fiber bundle within a glass tube.
Figure 3:
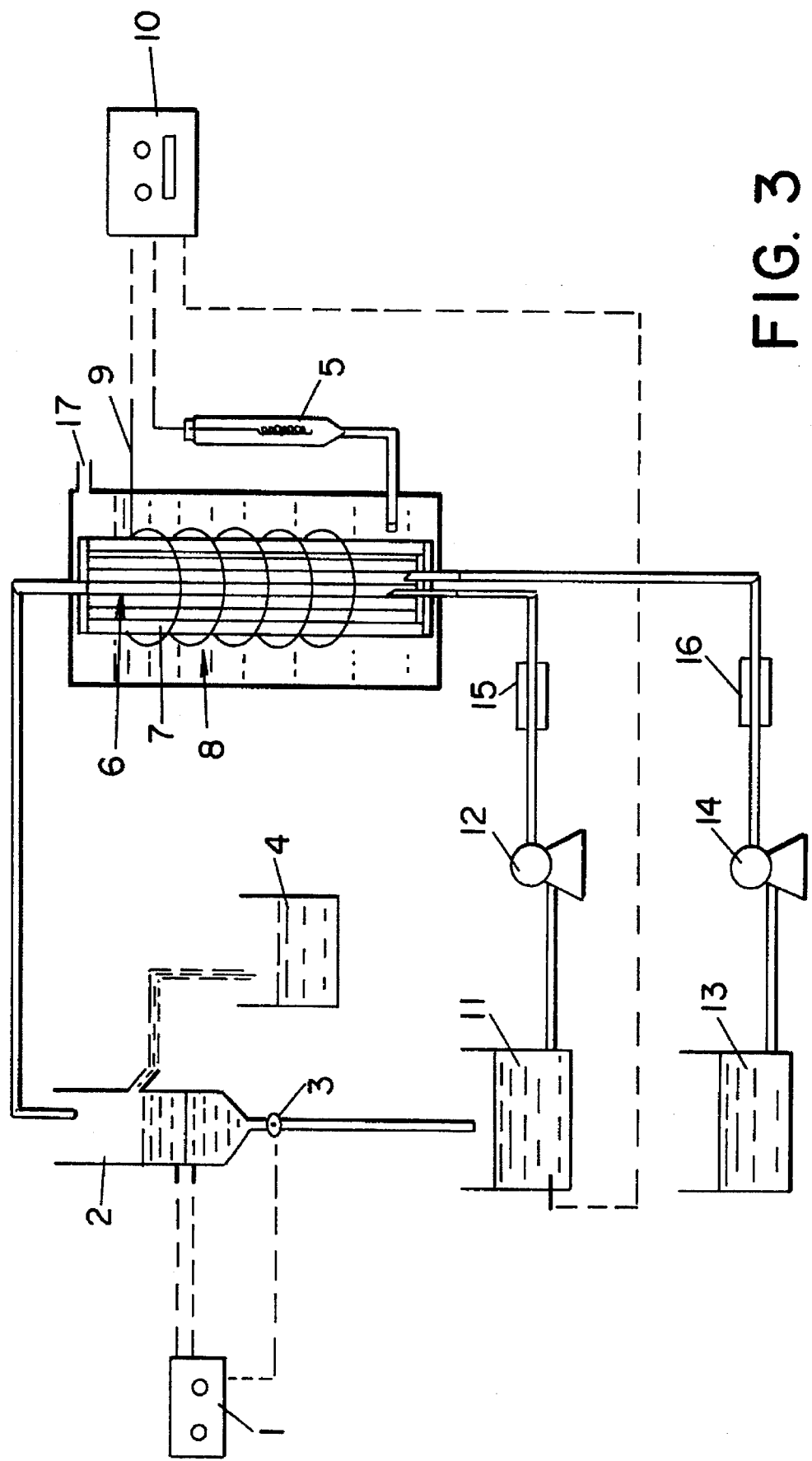
FIG. 3 illustrates the process of an electrolyzing apparatus having the vertical continuous capillary tube type mercury bundle electrode.

FIG. 3 is a schematic view of the electrolyzing apparatus according to the present invention. As shown in this drawing, a mercury-aqueous solution separator 2 on which a mercury level controller 1 is installed is connected to an aqueous solution storage tank 4. The mercury level controller 1 is connected to an electrolyzing apparatus which includes: a reference electrode 5, a capillary tube type mercury bundle 6, a porous glass tube 7, a counter solution 8 and a platinum electrode 9. The bottom of the electrolyzing apparatus is connected through a pump 12 to a mercury storage tank 11, and is also connected through a pump 14 to an aqueous solution storage tank 13.

In the drawing, reference code 3 indicates a solenoid valve, 10 indicates a potentiostat/data recording system, 15 and 16 indicate flow meters, and 17 indicates a gas-discharge hole.

In the present invention constituted as described above, the capillary tube type mercury bundle 6 which is used as a working electrode should be maintained as one continuum with a mercury storage tank through the mercury feeding line and the mercury supplying pump. The bundle 6 effects oxidizing/reducing reactions in which metal ions of the aqueous solution are oxidized or reduced on the surface of the mercury bundle by the electrons moved through the mercury storage tank 11.

The porous glass tube 7 isolates the capillary tube type mercury electrode, and the outside of the tube 7 is made to be filled by a counter electrode solution 8. Further, it has to be surrounded by the platinum wire 9 which serves as the counter electrode, while the reference electrode 5 is placed near the porous glass tube.

The counter solution chamber which contains the counter electrode solution is provided with a gas discharge hole 17, so that hydrogen or oxygen can be discharged.

The mixture of the aqueous solution and mercury, which is discharged from the capillary tube type mercury bundle, is separated into mercury and the aqueous solution by the mercury/solution separator 2. The mercury maintains a certain height by the solenoid valve 3 and by the mercury level controller 1. Further the mercury is circulated to the mercury storage tank 11, while the aqueous solution containing the metal ions of which oxidation state valances have been adjusted overflows over the surface of the mercury so as to be returned to the aqueous solution storage tank 4. The pumps 12 and 14 supply mercury and the aqueous solution to the capillary tube type mercury bundle, respectively. These pumps 12 and 14 have to have a capability of accurately supplying amounts of mercury and the aqueous solution, and have to have a sufficient outlet pressure$_{13}$ so that mercury and the aqueous solution can pass through the densely packed fiber bundle.

Under this condition, the flow rates of the aqueous solution and mercury greatly affect the electroredox experimental results such as the conversion yield of electroreaction, and oxidation/reduction limiting currents, and therefore, precise flow meters 15 and 16 have to be used.

Owing to the high surface tension, mercury can easily form a discontinuity within the circulating path. Therefore, the mercury system has to maintain an non-disconnected continuity, so that current can be stably supplied from the potentiostat 10 (which is connected to the mercury storage tank) through the mercury supplying line to the mercury capillary tube type fiber bundle.

Discontinuity in the mercury continuum from the mercury storge tank to the mercury capillary tube type bundle, which might bring about fatal results, is liable to occur just at the connection point between the mercury supplying line and the mercury capillary tube type bundle. Therefore the mercury capillary tube type bundle is required to be vertically positioned against the mercury supplying line so that the discontinuity can be prevented based on the self-gravity of mercury.

The pulses generated by the mercury supplying pump greatly impede the mercury continuity, and therefore, the pulses have to be eliminated as far as possible. If a pump generating the pulses has to be used, a buffer tank may be installed on the mercury supplying line so as to reduce the adverse influence of the pulses.

The interpretation on the oxidation and reduction reactions which proceed in the above described vertical circulating capillary tube type mercury bundle electrode can be carried out based on a simple formula, $I=nFf(C_{in}-C_{out})$. Further, the checking on the stability of the apparatus of the present invention can also be carried out based on the same formula. In the above formula, I indicates the current (in amperes) measured between the reference electrode and the capillary tube type mercury bundle electrode, and n indicates the number of electrons participated in the oxidation and reduction reactions. Further, F indicates the faraday constant (96,500 coulombs), f indicates the flow rate (liter/sec) of the aqueous solution, $C_{in}$ indicates the concentration (mole/liter) of the metal ions of the aqueous solution fed into the system, and $C_{out}$ indicates the concentration (mole/liter) of the metal ions of the aqueous solution coming out from the system.

When a sufficiently high potential is supplied to the system so that the oxidation/reduction reactions are carried out in limiting current state, the concentration of the metal ions becomes zero on the entire surface of the mercury. In this state, if the solution flows over the mercury capillary tube type bundle electrode surface for a certain time, the concentration outside the ion concentration gradient of the aqueous solution contacting with the mercury becomes zero. Consequently, the ion concentration of the aqueous solution coming out from the system, $C_{out}$, becomes zero, and therefore, the above formula becomes simpler, that is, $I=nFf\,C_{in}$.

This state is controlled by the residence time, that is, the time by which the solution stays within the mercury electrolyzing apparatus under a potential for controlling the oxidation valences state of the metal ions in the solution. This residence time can be adjusted by the flow rate of the solution, or by the length of the capillary tube type mercury bundle. Based on the above formula, the stability of the system, the analysis of the concentration and of the oxidation state of metal ion, and the research on the oxidation reduction reaction mechanism can be carried out.

Figure 4:
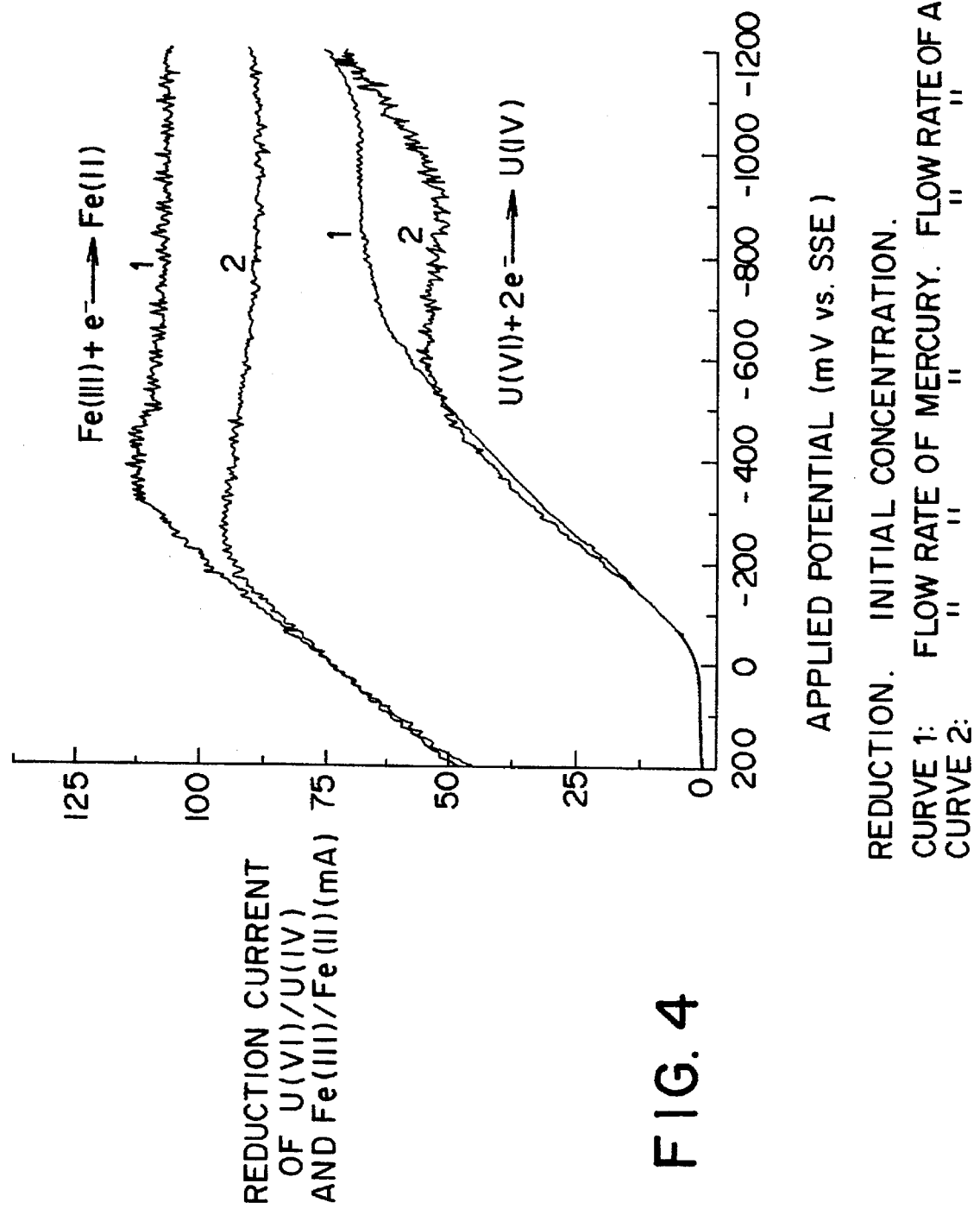
FIG. 4 shows the voltammograms for the reduction of ferric ions(+3), Fe(+3), and uranyl ion, U(+6), measured by the electrolyzing apparatus having the vertical continuous capillary tube type mercury bundle electrode.

FIG. 4 illustrates an example of reduction for the case of 1-electron reduction of Fe(+3)/Fe(+2) and for the case of 2-electron reduction of U(+6)/U(+4), in which the vertical circulating capillary tube type mercury bundle electrode according to the present invention is used.

This example was carried out in the following manner. That is, a glass tube having a length of 4 cm and an inside diameter of 0.8 cm was prepared. Then 1280 strands of polyester fibers (40s/2) was densely packed into the porous glass tube. The mercury was injected into the fibers, and thus, a vertical capillary tube type mercury bundle electrode electrolyzing apparatus was formed. Then at the same time, the U(+6) and Fe(+3) solutions of 2 g/l initial concentrations were fed, respectively. Then a scanning with 5 mV/sec(vs. Ag/AgCl reference electrode) was carried out. A voltammogram showing the reducing currents for uranium and iron is shown in FIG. 4.

In the respective reduction currents, small ripples looking like noises are seen in the curves. They are caused by the pulses of the mercury supplying pump, but do not affect significantly the analysis of the currents. The voltammograms show that the reduction limiting currents are well developed. According as the flow rate of the aqueous solution is increased, the potential which begins to show a limiting current moves toward the negative potential, and the limiting current is also increased.

Figure 5:
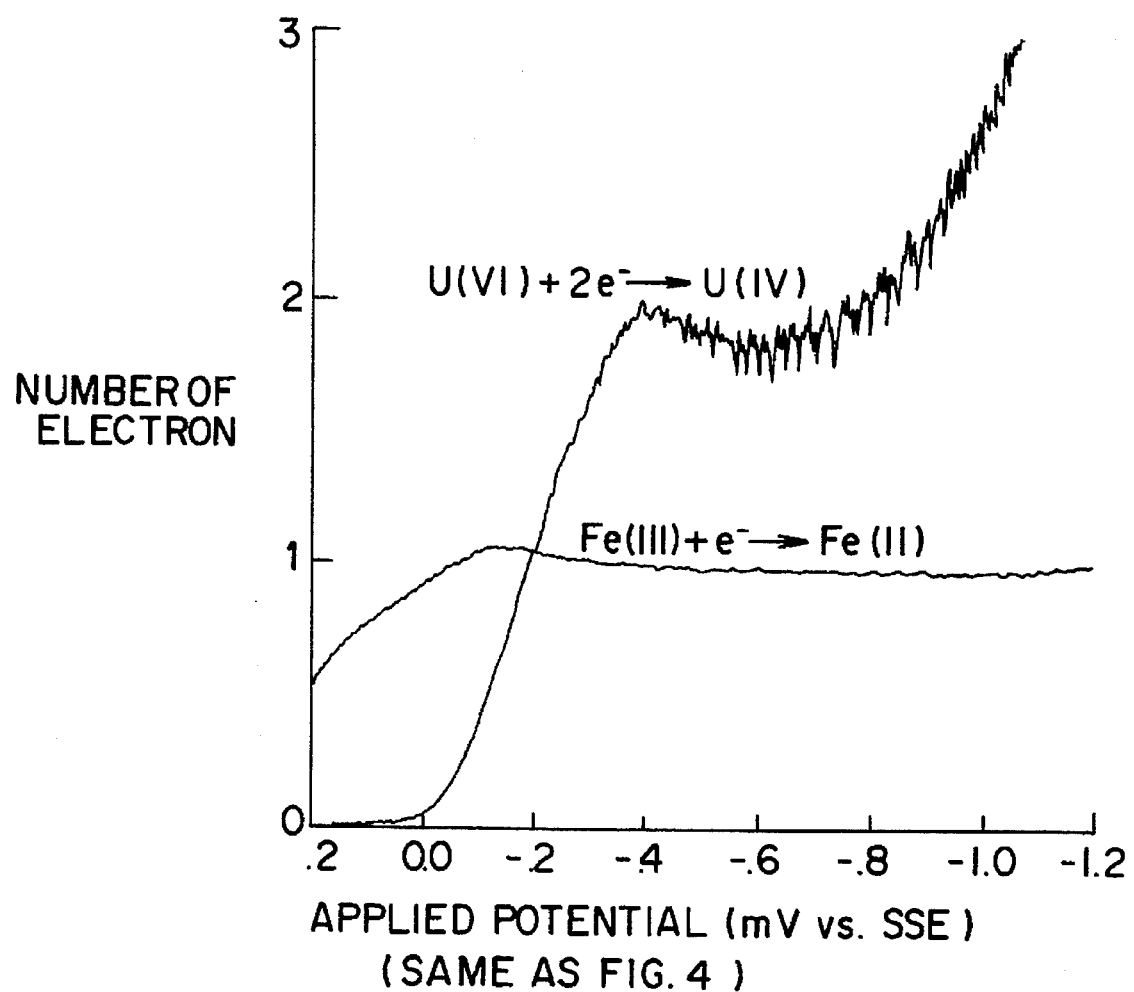
FIG. 5 shows the coulopotentiograms for the reduction of ferric ion and uranyl ion measured by the electrolyzing apparatus having the vertical continuous capillary tube type mercury bundle electrode.

FIG. 5 shows the coulopotentiograms expressed by the voltammograms of FIG.4 and the formula, I=nFf Cin, for the reductions of U(+6) and Fe(+3). In the reduction potential range showing the limiting current, the numbers of the electrons involved in the reduction reaction of the U(+6) and Fe(+3), which are calculated by using the known flow rate of the aqueous solution and the known initial concentration value, show exactly 2 and 1.

According to the present invention as described above, the vertical circulating capillary tube type mercury bundle electrode electrolyzing system can be expressed by I=nFf $C_{in}$. By using a small amount of continuously circulating mercury, the metal ions of the aqueous solution can be adjusted to the desired oxidation state continuously by 100%. Therefore, the electrolysis system is effective and stable enough to continuously and rapidly control the oxidation state of metal ions fed into the system under an appropriate aqueous flow rate, maintaining the property of high overpotential for the hydrogen evolution reaction. This system can be considered to be used for the study on electroredox mechanism and fast on-line analysis, etc.

What is claimed is:

1. A method for making a vertical circulating capillary tube mercury bundle electrode, comprising the steps of:

providing a porous glass tube;

densely inserting into said porous glass tube non-conductive fibers to form a fiber bundle, said fibers being stable to acid and alkaline solutions;

injecting mercury into said fibers with a pressure to overcome the surface tension of said mercury and to make said mercury have a capillary phenomenon within the densely packed fiber bundle, such that said mercury maintains a continuity within the fiber bundle, and is widely diffuse.

2. An electrolyzing method, comprising the steps of:

preparing an aqueous solution containing metal ions and requiring an oxidation state adjustment;

injecting said aqueous solution and mercury into a vertically installed capillary tube bundle;

making said aqueous solution diffuse together with said mercury within fibers of said bundle based on a capillary phenomenon, such that said aqueous solution is in contact with said mercury; and supplying an electric current from a mercury storage tank through a mercury supplying line to a mercury continuity body within said bundle, so as to make said aqueous solution in contact with said mercury and thereby adjust oxidation of the metal ions of said aqueous solution.

3. An electrolyzing method according to claim 2, further comprising the steps of:

using a separator to separate a mercury-aqueous solution from said capillary tube bundle into an oxidation state-adjusted aqueous solution and used mercury; and recirculating the used mercury to said mercury storage tank.

4. An electrolyzing apparatus comprising:

a mercury-solution separator with a mercury level controller installed thereon;

an aqueous solution storage tank connected to said mercury-solution separator;

an electrolyzing apparatus connected to said mercury level controller, and including: a reference electrode, a capillary tube mercury bundle, a porous glass tube, a counter electrolyte, and a platinum wire; and said electrolyzing apparatus having a bottom connected to a pump and thence to a mercury storage tank, and having the bottom connected to another pump and thence to said aqueous solution storage tank.

* * * * *